(12) United States Patent
Mallo et al.

(10) Patent No.: US 7,700,082 B2
(45) Date of Patent: Apr. 20, 2010

(54) SILYLATED POLYURETHANE-UREA COMPOSITIONS FOR USE IN COSMETIC APPLICATIONS

(75) Inventors: Richard A. Mallo, Woodbury, MN (US); Steven S. Kantner, St. Paul, MN (US); Kevin M. Lewandowski, Inver Grove Heights, MN (US); Larry R. Krepski, White Bear Lake, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/771,054

(22) Filed: Jan. 26, 2001

(65) Prior Publication Data

US 2002/0146382 A1   Oct. 10, 2002

(51) Int. Cl.
*A61Q 3/00* (2006.01)
*A61K 31/74* (2006.01)
*A61K 8/00* (2006.01)

(52) U.S. Cl. .................. 424/70.11; 424/401; 424/61; 424/78.03

(58) Field of Classification Search ............... 424/70.1, 424/70.12, 70.122, 84, 61, 69, 70.11, 70.7, 424/78.51, 63, 401, 45, 78.03, 78.37, 37, 424/42; 528/588, 28; 514/937
See application file for complete search history.

(56) References Cited

U.S. PATENT DOCUMENTS

| | | | | |
|---|---|---|---|---|
| 3,479,310 A | | 11/1969 | Dietrich et al. ............ 260/29.2 |
| 3,941,733 A | * | 3/1976 | Chang .................... 524/838 |
| 3,983,291 A | | 9/1976 | Chang .................... 428/290 |
| 4,567,228 A | * | 1/1986 | Gaa et al. .................. 524/588 |
| 4,738,992 A | | 4/1988 | Larson et al. ............... 521/157 |
| 4,872,867 A | * | 10/1989 | Joh ......................... 604/269 |
| 4,954,598 A | * | 9/1990 | Baghdachi et al. ............ 528/22 |
| 5,041,494 A | | 8/1991 | Franke et al. ............... 524/588 |
| 5,554,686 A | | 9/1996 | Frisch, Jr. et al. ........... 525/588 |
| 5,626,840 A | | 5/1997 | Thomaides et al. ...... 424/70.11 |
| 5,637,292 A | | 6/1997 | Thomas ...................... 424/61 |
| 5,643,581 A | | 7/1997 | Mougin et al. .............. 424/401 |
| 5,681,550 A | | 10/1997 | Rubino ....................... 424/61 |
| 5,756,633 A | | 5/1998 | Larson ....................... 528/28 |
| 5,919,860 A | | 7/1999 | Roesler et al. ............. 524/838 |
| 5,929,160 A | | 7/1999 | Krepski et al. ............. 524/590 |
| 5,932,652 A | * | 8/1999 | Roesler et al. ............. 524/839 |
| 5,952,445 A | | 9/1999 | Roesler et al. ............. 528/28 |
| 5,962,620 A | | 10/1999 | Reich et al. .................. 528/76 |
| 5,965,111 A | | 10/1999 | Ellingson et al. ............. 424/61 |
| 5,968,494 A | | 10/1999 | Kukkala et al. ............ 424/70.1 |
| 5,972,354 A | * | 10/1999 | de la Poterie et al. ........ 424/401 |
| 6,007,793 A | | 12/1999 | Bhatt et al. ................... 424/47 |
| 6,046,295 A | | 4/2000 | Frisch, Jr. et al. ............. 528/28 |
| 6,072,019 A | | 6/2000 | Sengupta ..................... 528/59 |
| 6,080,413 A | | 6/2000 | Ellingson et al. ............. 424/401 |
| 6,106,808 A | | 8/2000 | Bhatt et al. ................... 424/45 |
| 6,106,809 A | | 8/2000 | Bhatt et al. ................... 424/45 |
| 6,106,813 A | | 8/2000 | Mondet et al. ................. 424/61 |
| 6,111,010 A | | 8/2000 | Yu et al. ..................... 524/588 |
| 6,113,881 A | | 9/2000 | Bhatt et al. ................... 424/45 |
| 6,433,073 B1 | * | 8/2002 | Kantner et al. ............. 524/591 |
| 6,520,186 B2 | * | 2/2003 | Rollat et al. ................. 132/203 |
| 6,605,666 B1 | * | 8/2003 | Scholz et al. ............... 524/591 |

OTHER PUBLICATIONS

Rosthauser et al., "Waterborne Polyurethanes," *Advances in Urethane Science & Technology*, 10:121-162, 1987.
Poucher's Perfumes, Cosmetics & Soaps, 10th Ed. (2000), Hilda Butler, Ed., Kluwer Academic Publishers.

* cited by examiner

*Primary Examiner*—Blessing M Fubara

(57) ABSTRACT

A composition in the form of an aqueous dispersion used in cosmetic applications is provided. The composition comprises at least one polyurethane-urea polymer that is functionalized with at least one hydrolyzed or hydrolyzable silyl group. When the composition is used in hair care, it does not have a reshapable effect.

18 Claims, No Drawings

SILYLATED POLYURETHANE-UREA COMPOSITIONS FOR USE IN COSMETIC APPLICATIONS

TECHNICAL FIELD

The present invention relates to the use of silylated polyurethane-urea polymers in cosmetic applications.

BACKGROUND

It is common practice to use aqueous polyurethane-urea dispersions as a film forming resin in cosmetic and dermatological compositions as exemplified by recent patents in haircare (U.S. Pat. Nos. 5,626,840; 5,968,494; 6,007,793; 6,106,808; 6,106,809; and 6,113,881), skincare and makeup (U.S. Pat. Nos. 5,643,581; 5,962,620; and 5,972,354), and nailcare (U.S. Pat. Nos. 5,965,111; 6,080,413; and 6,106,813).

It is generally recognized that higher molecular weight polyurethane-urea polymers provide certain performance benefits to cosmetic formulations when compared to lower molecular weight polyurethane-urea polymers. It is generally believed that higher molecular weight materials have enhanced durability, abrasion resistance, and humidity resistance.

U.S. Pat. No. 6,106,808 (Bhatt et al.) discloses a hair spray composition comprising (1) about 0.25% to 6% of a carboxylated polyurethane resin having a weight average molecular weight of about 10,000 to 25,000, (2) 0% to about 6% of a second hair fixative resin; (3) 0% to about 80% of an alcohol; and (4) about 15% to 99% water. All percentages are by weight. It is stated that the carboxylated polyurethane resin provides an elastic, flexible film on hair giving it a natural feel. The second hair fixative resin functions to reduce flaking attributed to the carboxylated polyurethane resin and to impart stiffness to the hair spray composition.

U.S. Pat. No. 6,007,793 (Bhatt et al.) discloses another hair spray composition comprising (1) about 0.25% to 6% of a carboxylated polyurethane resin having a weight average molecular weight of about 15,000 to 150,000; (2) 0% to about 80% of an alcohol; and (3) about 15% to 95% water. All percentages are by weight. This patent, unlike U.S. Pat. No. 6,106,808, does not rely on optional second hair fixative resin and uses higher molecular weight carboxylated polyurethane resin.

Higher molecular weight polymer, however, generally translates to a higher viscosity, thus bringing with it possible difficulties in preparing aqueous polyurethane-urea dispersions. To reduce the viscosity, organic solvents can be used while preparing the aqueous dispersion. The solvents may need to be removed, adding steps and complexity to the formulation preparation. In a high viscosity formulation, it may be difficult to achieve dispersions with a small particle size. Such an effect tends to cause difficulty in forming smooth coalesced films in use, thereby reducing gloss and durability, among other properties. Some skilled in the art have used organic coalescing agents, possibly to ensure good film formation. See, e.g., U.S. Pat. No. 6,080,413 (Ellingson et al.) at column 6, starting at line 42. In cosmetic applications, the higher viscosity caused by high molecular weight polymers may lead to a draggy or greasy feel in use and during dry down.

Efforts have been made to provide the benefits and at the same time to minimize the drawbacks of using high molecular weight aqueous polyurethane-urea dispersions in cosmetic formulations. U.S. Pat. No. 5,637,292 (Thomas) delivers an aqueous dispersion of low molecular weight acrylated urethane oligomer and photoinitiator to the nail. The dispersion is dried, then cured using ultra-violet light to achieve a high molecular weight coating. The invention may require the use of an ultra-violet light source.

U.S. Pat. No. 5,681,550 (Rubino) adds 1 to 10% of hardening agents, such as epoxy resins or urethane polymers, to crosslink with the polyurethane-urea dispersion to achieve high molecular weight.

U.S. Pat. No. 5,965,111 (Ellingson et al.) discloses a fast-drying nail polish composition comprising (1) a film-forming, water-borne polymer; and (2) a liquid diluent. Various water-borne polymers are disclosed, including polyurethanes, polyacryls, and styrene-acryl copolymers. The film-forming polymers may be crosslinked to provide properties such as chip resistance and superior hardness. The patent discloses using multivalent metallic cations, such as $Zn^{+2}$, to ionically crosslink negatively charged moieties, such as sulfonates and carboxylates, either in the composition itself or after application and film formation.

A need exists for an aqueous polyurethane-urea dispersion which can be easily prepared and readily formulated into cosmetic and dermatological compositions for skin, nails, and hair to provide improved abrasion resistance, transfer resistance, and humidity resistance while providing excellent gloss, feel, and adhesion.

SUMMARY

The present invention provides aqueous polyurethane-urea dispersions containing terminal and/or pendant hydrolyzable and/or hydrolyzed silyl groups. Unlike the prior art, this invention does not rely on the use of a UV light source or the use of hardeners, which may lead to processing and handling problems as such limited pot life and potential toxicity problems. This invention also does not rely the use of multivalent metallic cations to ionically crosslink negatively charged moieties, such as sulfonates and carboxylates. Such cations may destabilize the dispersion may add unwanted color to the dried film. Furthermore, this invention does not rely on the use of organic coalescing agents. Such agents may have drawbacks, such as imparting an undesirable odor to the composition and a prolonged drying time to the film.

The inventive compositions are useful in cosmetic applications, providing improved resistance against abrasion, transfer, water, perspiration, and humidity while having excellent gloss, feel, and adhesion.

In brief summary, the invention provides for a composition in the form of an aqueous dispersion. The composition comprises at least one polyurethane-urea polymer that is functionalized with at least one hydrolyzed or hydrolyzable silyl group. The composition is used for cosmetic applications. When the cosmetic application is a hair care composition, the hair care composition does not have a reshapable effect.

The term "dispersion" means generally a two phase system where one phase contains discrete particles distributed throughout a bulk substance, the particles being the disperse or internal phase, and the bulk substance the continuous or external phase. In this invention, the continuous phase is the aqueous phase and at least a portion of the polymer exists as the discrete particle. Dispersions are possible through the use of certain components that are insoluble in the aqueous system. By "dispersion," it is also meant that not necessarily the entire polymer needs to be water insoluble; some of the polymer can be soluble in the water mixture. It is desirable that the dispersion remains stable under ambient conditions. Preferred dispersions are stable at room temperature for more than 30 days, preferably more than 90 days, more preferably for more than 180 days, and most preferably for more than 360 days.

The term "polyurethane-urea" means polymers containing urethane and/or urea groups. The term "hydrolyzable silyl group" means generally a silicon atom substituted with at least one moiety that will react with water to give a hydrolyzed silyl group. The term "hydrolyzed silyl group" means generally a silicon atom substituted with at least one —OH moiety. A polyurethane-urea that is functionalized with at least one hydrolyzed or hydrolyzable silyl group is also referred to as a silylated polyurethane-urea in this document.

Some inventive compositions, in film form, possess "self adhesion" properties because they preferentially adhere to themselves or a chemically similar material under pressure or force without the need for significantly elevated temperatures (e.g., without the need for temperatures above about 50° C.). Preferred inventive compositions exhibit self adhesion properties immediately upon contact to itself at room temperature (about 20° to 30° C.). As used in the previous sentence, the term "immediately" means less than a few minutes, e.g., about five minutes, preferably less than one minute, more preferably less than 30 seconds, depending on the application.

In one embodiment, composition exhibits self-adhesion properties when coated and dried to a film of about 0.025 millimeter in thickness.

The silylated polyurethane-urea has a low initial molecular weight and is believed to have the ability to build molecular weight and form lightly crosslinked films (as defined herein) on drying at room temperature. This feature makes the silylated polyurethane urea particularly useful in cosmetic applications. Cosmetic applications require some amount of water resistance, transfer resistance, or substantivity to skin, nails or hair.

Cosmetic applications include the following: (a) creams, emulsions, lotions, gels, and oils for the skin (hands, face, feet); (b) face masks (excluding chemical peeling products); (c) tinted bases (liquids, pastes, and powders); (d) make-up powders, after-bath powders, hygienic powders; (e) toilet soaps, deodorant soaps; (f) perfumes, toilet waters, cologne; (g) bath and shower preparations (salts, foams, oils, gels); (h) depilatories; (i) deodorants and antiperspirants; (j) hair care products (including hair tints and bleaches; products for waving, straightening and fixing hair; setting products; cleansing products such as lotions, powders, shampoos; conditioning products such as lotions, creams, and oils; hairdressing products such as lotions, lacquers, and brilliantines) but not reshapable hair styling compositions; (k) products for making-up and removing make-up from the face and the eyes; (l) products intended for application to the lips; (m) products for nail care and nail make-up; (n) products for external intimate hygiene; (o) sunbathing products; (p) products for tanning without sun; (q) skin-whitening products; and (r) anti-wrinkling products.

When the inventive dispersion is used in hair care products, the dispersion can provide faster drying and a volumizing effect. It can be used alone as a hair styling agent or used at low levels in combination with other hair styling resins to improve the humidity resistance. The hair care products, as described herein, are not "reshapable" hair styling compositions. "Reshapable" hair styling composition means a composition that can be restored or modified without new materials or heat being applied. For example, in order to restore or modify the hairstyle in case of "drooping" or loss of setting (dishevelment), no new materials, such as water or any form of fixing agent, or heat are required. The reshapable hairstyling composition can be long lasting, such as 10 to 24 hours, giving rise to a durable styling effect.

The inventive dispersion is useful by itself in cosmetic products or can be formulated with other ingredients known to the cosmetic industry to give cosmetic products containing an aqueous component. Such ingredients include emollients, humectants, other film forming polymers, propellants, pigments, dyes, buffers, organic and inorganic suspending and thickening agents, waxes, surfactants and cosurfactants, plasticizers, preservatives, flavoring agents, perfumes, and active ingredients including but not limited to sunscreen agents, insect repellents, vitamins, herbal extracts, antiperspirant and deodorant agents, skin or hair bleaching or coloring agents, depilating agents, antifungal and antimicrobial agents, anti-dandruff and antiacne agents, astringents, and corn, callus, and wart removers. The function of these ingredients, specific compounds providing these functions, and incorporation of these compounds into cosmetic products is well understood by those skilled in the art as, described in Poucher's Perfumes, Cosmetics and Soaps, 10th ed. (2000), Hilda Butler, Ed., Kluwer Academic Publishers, incorporated by reference.

DETAILED DESCRIPTION OF THE INVENTION

Various aqueous polyurethane-urea dispersions containing hydrolyzable or hydrolyzed silyl groups have been prepared by those skilled in the art. For example, U.S. Pat. Nos. 3,941,733; 3,983,291; 5,554,686; 5,756,633; 5,919,860; 5,952,445; 6,046,295; and 6,111,010 disclose preparation of water-dispersed polyurethane-urea polymers terminated with silane functionality suitable for use as coatings for leather, paper, wood, metals, ceramics, stone, concrete, straw, glass, porcelain, textiles, and plastics, and for use as binders, adhesives, and impregnants. U.S. Pat. No. 4,567,228 discloses aqueous dispersions of internally (i.e., pendant) silylated polyurethane-ureas and their use as coatings on hydroxyl-containing surfaces. U.S. Pat. No. 5,041,494 discloses aqueous dispersions of polyurethane-ureas that have terminal and/or pendant silane functionality for use as a coating composition on organic or inorganic substrates including glass, wood, metals, plastics, leather, paper, building materials, stone and rock.

Although aqueous dispersions of silylated polyurethane-ureas have been widely disclosed, the inventors are not aware of any references to their use as the film forming component in cosmetic compositions.

Processes and starting materials for preparing the aqueous dispersion of silylated polyurethane-ureas are disclosed in the references cited above. Suitable components for preparing the polyurethane-ureas include polyisocyanates (preferably diisocyanates); high molecular weight components (preferably a polyol); low molecular weight chain extenders containing hydroxy, hydrazide, or amine groups; compounds containing ionic or nonionic hydrophilic groups; and compounds containing silyl groups. Chain terminators can optionally be included to control molecular weight and reduce crosslink density in the final film.

One suitable method for preparing the polyurethane-urea involves reacting the polyisocyanates with polyols to form a prepolymer. The prepolymer can be chain extended followed by reaction with compounds containing silyl groups to form the polyurethane-urea polymer. The resulting polymers can then be used to formulate various cosmetic products.

Polyisocyanate Component

Any suitable organic polyisocyanate, aliphatic, cycloaliphatic, araliphatic or aromatic, can be used alone, or in combinations. While aromatic or aliphatic isocyanates are suitable, the aliphatic isocyanates generally give softer polymers and coatings that have better light stability than the aromatic isocyanates. Diisocyanates are one preferred class of polyisocyanate. Low levels of isocyanates containing more than two isocyanate groups in the molecule can be included without measurable changes in the characteristics of the resulting polymer. Suitable organic polyisocyanates include dicyclohexylmethane 4,4'-diisocyanate (commonly referred to as $H_{12}MDI$), 1,3-bis(isocyanatomethyl)cyclohexane, 1,3-bis(1-isocyanato-1-methylethyl)benzene (commonly referred to as TMXDI), 3,5,5-trimethyl-1-isocyanato-3-isocyanatomethylcyclohexane (commonly referred to as isophorone diisocyanate or IPDI), m-phenylene diisocyanate, p-phenylene diisocyanate, 2,4-tolylene diisocyanate, 2,6-tolylene diisocyanate, 4,4'-diisocyanato diphenylmethane (commonly referred to as MDI), benzidine diisocyanate, naphthalene-1,5-diisocyanate, hexamethylene diisocyanate (commonly referred to as HDI) and other alkylene diisocyanates (e.g., tetramethylene diisocyanate, decamethylene diisocyanate, and dodecamethylene diisocyanate), 4,4',4"-triphenylmethane triisocyanate, polyphenylmethylene polyisocyanates that are produced by phosgenation of aniline/formaldehyde condensation products containing up to about four aromatic rings, dianisidine diisocyanate, xylene diisocyanate, bis(2-isocyanatoethyl)fumarate, bis(2-isocyanatoethyl) cyclohex-4-ene-1,2-dicarboxylate, bis(2-isocyanatoethyl) carbonate, and many other organic polyisocyanates known in the art.

Polyol Component

In producing the inventive polyurethane-urea dispersions, one or more polyhydroxy compounds or polyols can be used in the reaction with the organic polyisocyanate described above.

Illustrative polyhydroxy compounds include the following classes of compounds: (a) lactone polyols and alkylene oxide adducts thereof, (b) polyester polyols, and alkylene oxide adducts thereof, (c) polyoxyalkylene polyols, polyoxycycloalkylene polyols, and alkylene oxide adducts thereof, and (d) polytetramethylene glycols.

Diols are one preferred class of polyols. The term "diol" is intended to include mixtures of diols as well as mixtures containing low levels of triols or tetrols that do not excessively affect the properties of the final product. Preferred diols are the polyester diols and polyoxyalkylene diols.

The term "alkylene oxide" includes, e.g., ethylene oxide, 1,2-epoxypropane, 1,2-epoxybutane, 2,3-epoxybutane, isobutylene oxide, epichlorohydrin, and the like and mixtures thereof.

Lactone polyols are prepared by reacting a lactone such as epsilon-caprolactone or a mixture of epsilon-caprolactone and an alkylene oxide with a polyfunctional initiator such as polyhydric alcohol. The term "lactone polyols" also includes the various copolymers such as lactone copolyesters, lactone polyester/polycarbonates, lactone polyester/polyethers, lactone polyester/polyether/polycarbonates, and the like.

Polyester polyols are esterification products that range from liquids to non-crosslinked solids, i.e., solids that are soluble in many of the more common inert normally liquid organic media. Polyester polyols are prepared by the reaction of polycarboxylic acids, their anhydrides, their esters or their halides, with a stoichiometric excess of a polyol. Illustrative of the polycarboxylic acids that can be used to prepare the polyester polyols preferably include dicarboxylic acids and tricarboxylic acids, such as maleic acid, succinic acid, glutaric acid, adipic acid, pimelic acid, suberic acid, azelaic acid, sebacic acid, chlorendic acid, 1,2,4-butane-tricarboxylic acid, phthalic acid, and the like. The esterification reaction is well known in the art.

Polyoxyalkylene polyols include alkylene oxide adducts of, e.g., water, ethylene glycol, diethylene glycol, propylene glycol, dipropylene glycol, glycerol, 1,2,6-hexanetriol, 1,1,1-trimethylol ethane or propane, pentaerythritol, and the like. The alkylene oxides used in producing polyoxyalkylene polyols normally have from 2 to 4 carbon atoms. Ethylene oxide, propylene oxide, and mixtures thereof are preferred.

Another useful class of polyols is the polyoxytetramethylene glycols, which are prepared by polymerizing tetrahydrofuran in the presence of acidic catalyst.

As indicated above, triols, tetrols, triisocyanates, etc., can be used in making the polyurethane-ureas used in the inventive dispersion. Small amounts of branching in the polyurethane-urea backbone improve adhesion and transfer resistance. Excessive amounts of branching can lead to excessive crosslinking and poor flow, leading to poor film formation. Preferably, there should not be more than 1 crosslink from polyol or polyisocyanate for each 3000 daltons. This amount of crosslinking is referred to as "light crosslinking" as used in this document. The unit "dalton" is defined as one-twelfth the mass of a neutral carbon-12 atom (or one-sixteenth the mass of an oxygen-16 atom) and is also referred to as the "atomic mass unit" (international). It is conveniently used in discussions of large molecules and is herein abbreviated as a capital letter D.

The molecular weight of the polyol component is one significant factor in determining the final properties of the polymer. Generally, the higher the molecular weight, the softer the resulting polymer. The term "molecular weight" is used herein to refer to the number average molecular weight ($M_n$). Polyols of molecular weight as low as 200 and as high as 5000 produce suitable polyurethane-urea polymer, molecular weight ranges of 300 to 3000 being preferred and most readily commercially available. Polyols of lower molecular weight can be used for chain extension as discussed below.

Chain Extender Component

As used herein the term "chain extender" means a polyactive hydrogen compound having a functionality of about 2 to 4, more preferably 2 to 3, and most preferably about 2 and generally having a molecular weight of about 30 to 2000, preferably 30 to 1000.

Preferred chain extenders are polyfunctional alcohols, amines, or carboxylic acid hydrazides. Most preferred chain extenders are polyfunctional amines and carboxylic acid hydrazides. Useful polyamines include ethylenediamine, 1,6-diaminohexane, piperazine, tris(2-aminoethyl)amine, and amine terminated polyethers such as JEFFAMINE D230 and JEFFAMINE D400, from the Huntsman Corporation, Salt Lake City, Utah. Useful carboxylic acid hydrazides include adipic acid dihydrazide and oxalic acid dihydrazide. Particularly useful polyfunctional alcohols include alkylene diols having 2 to 24 carbon atoms such as ethylene glycol, diethylene glycol, 1,4-butane diol, 1,8-octane diol, and 1,2-decandiol.

Other useful chain extenders include polythiols such as 1,2-ethanedithiol, 1,4-butanedithiol, 2,2'-oxytris(ethane thiol), and di- and tri-mercaptopropionate esters of poly(oxyethylene) diols and triols. Water is also useful as a chain extender as it reacts with isocyanate to form an unstable carbamic acid, which loses carbon dioxide to liberate an amine. This amine is then available to react with another isocyanate.

In one embodiment, the chain extender is selected from the group consisting of water; ethylenediamine; 1,6-diaminohexane; piperazine; tris(2-aminoethyl)amine; amine terminated polyethers; adipic acid dihydrazide; oxalic acid dihydrazide; ethylene glycol; 1,4-butane diol; 1,8-octane diol; 1,2-ethanedithiol; 1,4-butanedithiol; 2,2'-oxytris(ethane thiol); di- and tri-mercaptopropionate esters of poly(oxyethylene) diols and triols; and mixtures thereof.

Hydrophilic Component

The polyurethane-urea can be dispersed in water through the use of external surfactants or, more preferably, by incorporating a hydrophilic group into the polymer. The latter is achieved using a hydrophilic component having at least one water solubilizing group and at least one isocyanate reactive functional group. The hydrophilic component acts primarily to stabilize the polyurethane-urea dispersion in an aqueous solvent system. Suitable hydrophilic groups are those that contain an ionic group or a moiety capable of forming an ionic group or a nonionic water soluble group such as polyethylene glycol and its copolymers with propylene glycol.

When present, the ionic group of the hydrophilic component can be cationic, anionic, or zwitterionic. The cationic groups may originate from the isocyanate or polyol component but most conveniently are added in as a polyol component. The cationic group may be incorporated directly into the prepolymer. For example, a quaternary diol such as VARIQUAT 1215 may be reacted into the prepolymer directly. Alternatively, a precursor group can be reacted into the prepolymer and then be rendered cationic in a subsequent reaction. For example, active hydrogen functional tertiary amines such as methyldiethanolamine and its polyethoxylated adducts may be incorporated into the prepolymer backbone and subsequently protonated with a mineral or organic acid to form an ionic salt or alkylated to form a quaternary ammonium group. Reaction of the incorporated tertiary amine with hydrogen peroxide, propane sultone or lactone gives zwitterionic moieties. Preferred stabilizing cationic components are very water soluble, generally have a solubility in water of at least 1% by weight and preferably in excess of 10% by weight. Preferred stabilizing cationic compounds have the following structure:

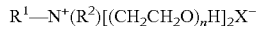

where $R^1$ is $C_1$ to $C_{18}$ alkyl or $C_6$ to $C_{18}$ aryl or aralkyl optionally substituted in available positions in or on the chain by N, O, and S;

$R^2$ is hydrogen or $C_1$ to $C_{18}$ alkyl;

n is an integer from about 1 to 200, preferably 1 to 50, and most preferably 1 to 20; and X is halogen, sulfate, methosulfate, ethosulfate, acetate, carbonate, phosphate.

Preferred cationic stabilizing compounds include protonated and alkylated methyl diethanol amine as well as PEG 2 cocomonium chloride and PEG-15 cocomonium chloride available from CKWitco, Greenwich, Conn. as VARIQUAT 638 and VARIQUAT K1215 respectively.

It is possible to incorporate cationic compounds that have a single reactive hydrogen group. However, they are less preferred.

The anionic stabilizer used in the present invention can be present on either the isocyanate component or the polyol component. Typically, and most conveniently, the anionic stabilizer is present as the polyol component. The anionic group can be sulfonate, phosphonate, phosphate, and carboxylate but is preferably either sulfonate or carboxylate and most preferably a sulfonate. The most preferred sulfonates are the sulfonated polyols described in U.S. Pat. No. 4,738,992 (Larson et al.). Particularly preferred sulfonates are polyesterdiols having the following structure:

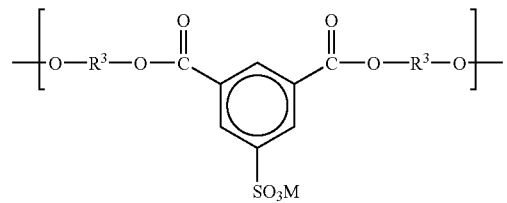

wherein each $R^3$ is independently a divalent aliphatic group having an average molecular weight of 200 to 600 comprising ether or ester functional groups selected from the group consisting of:

—CH$_2$CH$_2$—(OCH$_2$CH$_2$—)$_n$—,

—CH(CH$_3$)CH$_2$—(OCH(CH$_3$)CH$_2$—)$_n$—,

—(CH$_2$)$_4$—(O(CH$_2$)$_4$)$_n$—, and

—(CH$_2$)$_m$CO—[O(CH$_2$)$_m$CO]$_n$—groups; and mixtures thereof;

where m is an integer from about 2 to 5 and n is an integer from about 2 to 15;

and M is a cation, preferably M is Na, but M can be H, K, Li, or a primary, secondary, tertiary, or quaternary ammonium cation and mixtures thereof such as ammonium, methylammonium, butylammonium, diethylammonium, triethylammonium, tetraethylammonium, and benzyltrimethyl-ammonium cation and mixtures thereof.

Suitable carboxylate and carboxylic acid functional polyols include dimethylolpropionic acid and its polyethoxylated derivatives as well as acid grafted polyethers such as the UCARMOD polyols available from Union Carbide Specialty Chemicals Div., Danbury, Conn. Carboxy functional polyamines, such as lysine and histidine are also useful. These can be neutralized with an organic or inorganic base either before or after preparation of the prepolymer.

Silyl Containing Component

The silyl group can be incorporated into the polyurethane-urea polymer terminally (at the ends), internally (pendant from the backbone), or a combination of the two. When incorporated terminally, a component containing at least one silyl group and one electrophilic or nucleophilic reactive group can be used. For example, a prepolymer terminated with isocyanate can be reacted with a silane functionalized with an alkyl amine, hydroxyl, or thiol.

Representative isocyanate-reactive silanes include, but are not limited to the following compounds:

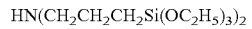

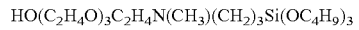

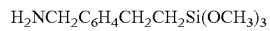

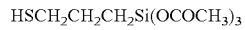

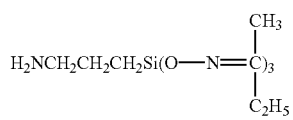

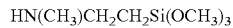

and mixtures thereof.

Conversely, a prepolymer terminated with an amine or a hydroxyl moiety can be reacted with a component containing a silane that is functionalized with an alkyl isocyanate such as 3-isocyanatopropyltriethoxysilane.

When incorporated internally, a component containing at least one silyl group and at least two isocyanate or isocyanate reactive groups can be used. For example, silanes functionalized with two hydroxyls or two amines can be used as chain extenders, placing silane functionality internally.

Representative isocyanate-reactive silanes with two reactive sites include:

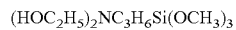

Alternatively, a silane with only one electrophilic or nucleophilic group can be used, provided that the polymer possesses a companion nucleophilic or electrophilic group along its backbone. For example, a pendant carboxylic acid functionality on the polymer chain can be reacted with an alkyl epoxy silane such as 3-glycidoxypropyltrimethoxysilane.

Other methods of incorporating silyl groups are known in the art, such as hydrosilation of a pendant or terminal olefin with a trialkoxysilane hydride.

Silane compounds containing two or three hydrolyzable groups on the silicon (as $X_2Si=$ or $X_3Si—$) and one or two organic groups are suitable for forming the silyl groups. It is preferred to have three hydrolyzable groups on the silicon. The "X" can be any of the conventional hydrolyzable groups, such as hydrogen, alkoxy, acyloxy, halogen, amino, oxime and the like. The alkoxy group is the most preferred hydrolyzable group and particularly preferred compounds are thus of the structure $(R^4O)_3SiR^5Z$, wherein $(R^4O)_3SiR^5—$ is a silyl moiety. $R^4$ is lower alkyl radical of one to four, preferably one or two carbon atoms (i.e., methoxy, ethoxy), or lower acyl of 2 to 5, preferably 2 or 3 carbon atoms (i.e., acetyl or propionyl). $R^5$ is divalent organic bridging radical of 2 to 20, preferably 3 to 10 carbon atoms selected from the group consisting of (1) divalent hydrocarbyl radical free from olefinic unsaturation and free from isocyanate-reactive groups, (2) divalent polyoxyalkylene mono- or poly-oxaalkylene radical containing not more than one ether oxygen per two carbon atoms, and (3) divalent hydrocarbylamino radical. Z is a nucleophilic group such as —OH, —SH, —NHR, —$NH_2$, and —$N(C_2H_4OH)_2$ or an electrophilic group such as —NCO and epoxide. Representative divalent alkylene radicals include —$CH_2CH_2$—, —$CH_2CH_2CH_2$—, —$CH_2CH_2OCH_2CH_2$—, —$CH_2CH_2CH_2$ NH$CH_2CH_2$—, —$CH_2CH_2C_6H_4CH_2CH_2$—. Such silicon-containing compounds are well known in the art and many are commercially available or are readily prepared.

Sufficient amount of silane should be present to provide the desired level of water resistance and film properties. In general, these levels are attained with polymers containing, on the average, no more than two silicon atoms per 1000 daltons and no less than two silicon atoms per 125,000 daltons. The preferred range is two silicon atoms (or silyl groups) per 1500 to 100,000 daltons.

It is believed that the chain-extended silyl-functional polyurethane-ureas cure by hydrolysis of the silyl group and formation of siloxane linkages. This reaction probably begins as soon as the polymer is exposed to water, but generally proceeds slowly at room temperature and within a pH range of about 6.5 to 9. The reaction proceeds more rapidly after drying and is accelerated in the presence of acidic or basic catalysts. The formation of siloxane linkages crosslinks the film formed from the polymer. These crosslinks are distinguished from crosslinks formed in low concentration from the use of triols, triisocyanates, tetrols, and other highly functional reactants in preparing the prepolymer. The latter crosslinks are herein sometimes referred to as prepolymer-derived crosslinks and are to be understood as the type of crosslinks present before curing.

Chain Terminator Component

As used herein the term "chain terminator" means an active hydrogen compound having a functionality of about 1 and generally having a molecular weight of about 30 to 2000, preferably about 30 to 1000. It can be included during preparation of the prepolymer or added during the dispersion and chain extension step. Preferred chain terminators are monofunctional alcohols, amines, or carboxylic acid hydrazides. When chain termination is done during the dispersion step, the most preferred chain terminators are monofunctional amines because the isocyanate functional moieties will selectively react with them in the presence of water. Useful amines include butyl amine and 2-amino-2-methyl-1-propanol. Useful monofunctional alcohols include those having 2 to 24 carbon atoms such as ethanol, butanol, octanol, cetyl alcohol, and stearyl alcohol.

Dispersion Techniques

Aqueous dispersions of the polyurethane-urea may be prepared in accordance with the methods known in polyurethane chemistry and described, e.g., in "Waterborne Polyurethanes," Rosthauser et al., Advances in Urethane Science and Technology, Vol. 10, pg. 121-162 (1987).

These methods generally involve subjecting the polyurethane-urea to a high shear process in the presence of an aqueous carrier. Microfluidization is one such process for making stable uniform sub-micron dispersions, including dispersions of polyurethane-ureas. The process uses high-pressure liquid jet milling to combine water dispersible polymers with water. The polymers generally should have a viscosity in the range of 1 to 500,000 centipoises using a Brookfield viscometer with an appropriate spindle and speed to give readings in the 20 to 80 range. The viscosity measurement typically takes place at room temperature of about 25° C. When higher viscosity is encountered, an organic solvent may be added to reduce the viscosity to the desired range. In the microfluidization process, the polyurethane-urea or solution of polyurethane-urea in organic solvent can be injected into a water stream and then subjected to high pressure of 0.6 to 300 MPa (100 to 40,000 psi) liquid jet milling in interaction chambers. The interaction chambers, which provide a high shear zone, are generally configured to be explosive expansion chambers, or use high velocity impinging streams, or contain a series of orifices in series having decreasing diameters. In this process, all of the liquid is forced through the interaction chamber configurations providing uniform shear for all the material.

When organic solvent is used to aid in preparation of the polyurethane-urea and reduce viscosity, it is preferable that this solvent is miscible with water allowing for dispersion into an aqueous solution. If the organic solvent having a boiling point lower than 100° C. has been used, the organic solvent may be evaporatively removed to leave an essentially aqueous polymer dispersion of the silylated polyurethane-urea. Representative organic solvents useful for this process include acetone, methyl ethyl ketone, and tetrahydrofuran. An organic solvent that has a boiling point greater than 100° C. (referred to as "high boiling solvent" for convenience) can also be used, but is not preferred. When high boiling solvent is used, the preparation should be conducted in as concentrated solution as possible, e.g., preferably equal to or less than 20 weight percent solvent to minimize the amount present in the dispersion. Such high boiling solvents should be selected from materials that do not have toxicity or irritancy concerns in cosmetic application. Of course, solvents with boiling points lower than 100° C., such as ethanol, can optionally be included in the final formulation to provide benefits such as fast-drying.

According to one process for preparing the polyurethane-urea dispersions, an isocyanate-functional prepolymer is prepared, chain extended and/or chain terminated to form a polyurethane-urea and subsequently dispersed in water. This process is disclosed in U.S. Pat. No. 3,479,310.

When amines are reacted with the isocyanate-functional prepolymer either as chain terminators or chain extenders, a preferred method of preparing the dispersion is by dispersing the prepolymer in water. The prepolymer is then reacted with the amino group-containing compounds, which may be mixed with water either before, during or after dispersing the isocyanate-functional prepolymer.

The amount of amino group-containing compounds to be used in accordance with the present invention is dependent upon the number of isocyanate groups in the prepolymer. Generally, the ratio of isocyanate groups amino groups is 1.0:0.6 to 1.0:1.1, preferably 1.0:0.8 to 1.0:0.98 on an equivalent basis.

The reaction between the isocyanate-functional prepolymer and the amino group-containing compounds is generally conducted at temperatures of about 5° to 90° C., preferably about 20° to 80° C., and more preferably about 30° to 60° C. The reaction conditions are normally maintained until the isocyanate groups are essentially completely reacted.

The final product is a stable, aqueous dispersion of polyurethane-urea particles having a solids content of up to about 60%, preferably about 15% to 60%, and more preferably about 30% to 45% by weight. It is always possible, however, to dilute the dispersions to any minimum solids content desired. The average particle size of the polyurethane-urea is generally below about 1.0 micron, preferably about 0.001 to 0.5 micron and more preferably about 0.01 to 0.3 micron. The small particle size enhances the stability of the dispersed particles and also leads to films with high surface gloss. The dispersions may be blended with other dispersions or with other known additives such as fillers, plasticizers, pigments, carbon black, silica sols and the known leveling agents, wetting agents, antifoaming agents, and stabilizers.

EXAMPLES

The following examples are provided to illustrate different embodiments and details of the invention. Although the examples serve this purpose, the particular ingredients and amounts used as well as other conditions and details are not to be construed in a manner that would unduly limit the scope of this invention. Unless otherwise specified, all percentages are in weight percent.

| Abbreviations | |
|---|---|
| Components | Manufacturer |
| absolute ethanol | Aaper Alcohol and Chemical, Shelbyville, KY |
| acetone | J. T. Baker, Inc., Phillipsburgh, NJ |
| butylamine | Aldrich Chemical Co., Milwaukee, WI |
| cetearyl alcohol | Henkel Corp., Cincinnati, OH |
| cetyl alcohol | Croda, Inc., Parsippany, NJ |
| dibutyltin dilaurate (DTDL) | Aldrich Chemical Co., Milwaukee, WI |
| diethylene glycol | Aldrich Chemical Co., Milwaukee, WI |
| disodium ethylenediaminetetraacetic acid (EDTA(N$_2$)) | W.R. Grace and Co., Nashua, NH |
| ethyl paraben | Aldrich Chemical, Milwaukee, WI |
| ethylene glycol (EG) | Aldrich Chemical Co., Milwaukee, WI |
| ethylene glycol distearate | Uniqema, Wilmington, DE |
| glycerin | Aldrich Chemical, Milwaukee, WI |
| glyceryl monostearate SE | Henkel Corp., Cincinnati, OH |
| isophorone diisocyanate (IPDI) | Aldrich Chemical Co., Milwaukee, WI |
| methyl ethyl ketone (MEK) | J. T. Baker, Inc., Phillipsburgh, NJ |
| methyl paraben | Aldrich Chemical, Milwaukee, WI |
| octadecamethylcyclotetrasiloxane | Dow Corning, Midland, MI |
| octadecanol | Proctor and Gambel, Cincinnati, Ohio |
| octyl palmitate | Stepan Chemical, Northfield, IL |
| polycaprolactone diol | TONE 0201 diol, Union Carbide, Dansbury, CT |
| polycaprolactone sodium sulfo isophthalate (PCPSSIP) | Prepared according to Example 29 of U.S. Pat. No. 5,929,160 |
| propyl paraben | Aldrich Chemical, Milwaukee, WI |
| propylene glycol (PG) | Aldrich Chemical Co., Milwaukee, WI |
| stearic acid | Aldrich Chemical Co., Milwaukee, WI |
| stearyl alcohol | Croda, Inc. Parsippany, NJ |
| triethanol amine | Aldrich Chemical Co., Milwaukee, WI |
| triethylamine | Aldrich Chemical Co., Milwaukee, WI |
| 1,2-decanediol | Aldrich Chemical Co., Milwaukee, WI |
| 1,6-diisocyanatohexane | Aldrich Chemical Co., Milwaukee, WI |
| 2,2'-bis(hydroxymethyl)propionic acid | Aldrich Chemical Co., Milwaukee, WI |
| 3-aminopropyltriethoxysilane | Aldrich Chemical Co., Milwaukee, WI |
| 4,4'-diisocyanato dicyclohexylmethane | Aldrich Chemical Co., Milwaukee, WI |

-continued

| Abbreviations | |
|---|---|
| Components | Manufacturer |
| N-(3-(trimethoxysilyl)propyl)ethylenediamine | Gelest, Inc., Tullytown, PA |
| Abil ™ EM90 | Goldschmidt, Hopewell, VA |
| Arlacel ™ C | ICI Americas, Wilmington, DE |
| Brij ™ 30 | ICI Americas, Wilmington, DE |
| Candelilla #1 | Frank B. Ross Co., Jersey City, NJ |
| Carnauba #1 | Frank B. Ross Co., Jersey City, NJ |
| Cocamide MEA | Rhodia, Cranbury, NJ |
| Finsolv ™ TN | Finetex Co., Elmwood Park, NJ |
| Germaben II ™ | Sutton Laboratories, Chatham, NJ |
| Incronam ™ 30 | Croda, Inc., Parsippany, NJ |
| Lauriciden ™ | Med-Chem Labs Inc., East Lansing, MI |
| Lipomulse ™ 165 | Lipo Chemicals, Inc., Paterson, NJ |
| Miranol ™ CS | Rhodia, Cranbury, NJ |
| Monosil ™ PLN | ICI Americas, Wilmington, DE |
| Natrosol ™ 250 MR, HEC | Aqualon, Wilmington, DE |
| Neutrol ™ TE | BASF Corp, Mount Olive, NJ |
| Octocrylene | BASF Corp. Mount Olive, NJ |
| PEG 150 tetrastearate | Croda, Inc., Parsippany, NJ |
| Pemulen ™ TR-1 (2% solution) | Goodrich Performance Materials, Cleveland, OH |
| Phenonip ™(TM) | Nipa Hardwicke Inc., Wilmington, DE |
| PVP K-30 | ISP, Wayne, NJ |
| Rhapsody ™ 1 M | Ultra Chemical, Red Bank, NJ |
| Standapol ™ A | Henkel Corp., Hoboken, NJ |
| Standapol ™ EA-2 | Henkel Corp., Hoboken, NJ |
| Stepanmild ™ RM-1 | Stepan Chemical, Northfield, IL |
| Tween ™ 80 | ICI Americas, Wilmington, DE |
| Veegum ™ | R.T. Vanderbelt, Norwalk, CT |
| Z-Cote ™ HP-1 | Sunsmart Inc., Wainscott, NY |
| black iron oxide | Cardre, Inc., South Plainfield, NJ |
| jojoba oil | Purcell Natural Jojoba, Avila Beach, CA |
| mineral oil | Witco Co., Houston, TX |
| red iron oxide #70421 | Cardre, Inc, South Plainfield, NJ |
| teatree oil | Jason Natural Cosmetic (Culver City, CA) |
| titanium dioxide #70429 | Cardre, Inc, South Plainfield, NJ |
| yellow iron oxide #70422 | Cardre, Inc, South Plainfield, NJ |
| white beeswax | Frank B. Ross Co., Jersey City, NJ |
| FD&C yellow 6 | Warner-Jenkinson, South Plainfield, NJ |
| FD&C Blue 1 | Warner-Jenkinson, South Plainfield, NJ |
| 3M brand Silicones "Plus" Polymer SA 70 in D5 | 3M Co., St. Paul, MN |
| 3M brand Silicones "Plus" Polymer VS 80 | 3M Co., St. Paul, MN |

Example 1

Preparation of Silanol Terminated Polyurethane-urea in Water

A mixture of PCPSSIP (349.7 g and 0.47 mol, based on a hydroxyl equivalent weight of 370 for the mixture), polycaprolactone diol (39.3 g, 0.08 mol), ethylene glycol (69.9 g, 1.13 mol), diethylene glycol (23.9 g, 0.23 mol), IPDI (450.1 g, 2.03 mol), DTDL (0.90 g, 1.4 mmol), and MEK (502 g) was charged to a vessel equipped with stirring and heated to 80° C. After 4 hours, a solution of 3-aminopropyltriethoxysilane (49.9 g, 0.23 mol) in MEK (473 g) was added to the reaction mixture, which was maintained at 80° C. for an additional 15 minutes. Water (975 g) was added to the reaction mixture over a 15 minute period with vigorous stirring and MEK was subsequently distilled from the mixture under reduced pressure to produce a dispersion (50% solids) of a silanol terminated polyurethane-urea in water.

Example 2

Preparation of Silanol Terminated Polyurethane-urea in Water

A mixture of PCPSSIP (29.21 kg, 43.0 mol based on a hydroxyl equivalent weight of 340 for the mixture), polycaprolactone diol (10.75 kg, 20.5 mol), ethylene glycol (5.10 kg, 82.1 mol), IPDI (34.9 kg, 157.0 mol), DTDL (127 g, 0.20 mol) and MEK (43 kg) was heated with stirring to 80° C. After 4 hours, a solution of 3-aminopropyltriethoxysilane (4.75 kg, 21.5 mol) in MEK (43 kg) was added to the reaction mixture, which was maintained at 80° C. for an additional 15 minutes. Water (136 kg) was added to the reaction mixture over a 15 minute period with vigorous stirring and MEK was subsequently distilled from the mixture under reduced pressure to produce a dispersion (43% solids) of a silanol terminated polyurethane-urea in water. Modulated differential scanning calorimetry (MDSC) and tensile properties analyses made of a film of the dispersion indicated that the polymer had a $T_g$ of 30° C. and a tensile strength of 4536 psi at 236% elongation.

Example 3

Preparation of Silanol Terminated Polyurethane-urea in Water

A mixture of 1,2-decanediol (69.71 g, 0.40 mol), 1,6-diisocyanatohexane (102.94 g, 0.61 mol), DTDL (0.27 g, 0.4 mmol) and acetone (161 mL) was heated with stirring to 55° C. After 2 hours, PCPSSIP (125.8 g, 0.17 mol based on a hydroxyl equivalent weight of 370 for the mixture) was added, and the mixture was heated for 2 additional hours at 55° C. A solution of 3-aminopropyltriethoxysilane (9.79 g, 0.044 mol) in acetone (144 mL) was added to the reaction mixture, which was maintained at 55° C. for an additional 15 minutes. Water (500 mL) was added to the reaction mixture over a 15 minute period with vigorous stirring and acetone was subsequently distilled from the mixture under reduced pressure to produce a dispersion of a silanol terminated polyurethane-urea in water. MDSC and tensile properties analyses made of a film of the dispersion indicated that the polymer had a $T_g$ of −17° C. and a tensile strength of 642 psi at 806% elongation.

Example 4

Preparation of Silanol Terminated Polyurethane-urea in Water

A mixture of 1,2-decanediol (34.86 g, 0.20 mol), 1,6-diisocyanatohexane (51.47 g, 0.31 mol), DTDL (0.14 g, 0.2 mmol) and acetone (80 niL) was heated with stirring to 55° C. After 2 hours, PCPSSIP (62.9 g, 0.09 mol based on a hydroxyl equivalent weight of 370 for the mixture) was added, and the mixture was heated for 2 additional hours at 55° C. A solution of 3-aminopropyltriethoxysilane (20.6 g, 9.3 mmol) and butylamine (0.45 g, 6.2 mmol) in acetone (69 mL) was added to the reaction mixture, which was maintained at 55° C. for an additional 15 minutes. Water (240 mL) was added to the reaction mixture over a 15 minute period with vigorous stirring and acetone was subsequently distilled from the mixture under reduced pressure to produce a dispersion of 15 a silanol terminated polyurethane-urea in water.

Example 5

Preparation of Silanol Terminated Polyurethane-urea in Water

A mixture of 1,2-decanediol (22.05 g, 0.13 mol), 1,6-diisocyanatohexane (32.56 g, 0.19 mol), DTDL (0.09 g, 0.1 mmol) and acetone (51 mL) was heated with stirring to 55° C. After 2 hours, PCPSSIP (0.05 mol based on a hydroxyl equivalent weight of 370 for the mixture) was added, and the mixture was heated for 2 additional hours at 55° C. A solution of 3-aminopropyltriethoxysilane (1.97 g, 8.9 mmol) and butylamine (0.22 g, 3.0 mmol) in acetone (45 mL) was added to the reaction mixture, which was maintained at 55° C. for an additional 15 minutes. Water (160 mL) was added to the reaction mixture over a 15 minute period with vigorous stirring and acetone was subsequently distilled from the mixture under reduced pressure to produce a dispersion of a silanol terminated polyurethane-urea in water.

Example 6

Preparation of Silanol Terminated Polyurethane-urea in Water

A mixture of 1,2-decanediol (24.28 g, 0.12 mol), 1,6-diisocyanatohexane (31.79 g, 0.19 mol), DTDL (0.08 g, 0.1 mmol) and acetone (52 mL) was heated with stirring to 55° C. After 2 hours, PCPSSIP (40.9 g, 0.06 mol based on a hydroxyl equivalent weight of 370 for the mixture) was added, and the mixture was heated for 2 additional hours at 55° C. A solution of 3-aminopropyltriethoxysilane (1.12 g, 5.1 mmol) and butylamine (0.37 g, 5.1 mmol) in acetone (45 mL) was added to the reaction mixture, which was maintained at 55° C. for an additional 15 minutes. Water (130 mL) was added to the reaction mixture over a 15 minute period with vigorous stirring and acetone was subsequently distilled from the mixture under reduced pressure to produce a dispersion of a silanol terminated polyurethane-urea in water.

Example 7

Preparation of Silanol Terminated Polyurethane-urea in Water

A mixture of 1,2-decanediol (27.88 g, 0.16 mol), 1,6-diisocyanatohexane (41.18 g, 0.24 mol), DTDL (0.11 g, 0.2 mmol) and acetone (64 mL) was heated with stirring to 55° C. After 2 hours, PCPSSIP (50.32 g, 0.07 mol based on a hydroxyl equivalent weight of 370 for the mixture) was added, and the mixture was heated for 2 additional hours at 55° C. A solution of 3-aminopropyltriethoxysilane (2.15 g, 9.7 mmol) and butylamine (0.30 g, 4.2 mmol) in acetone (55 mL) was added to the reaction mixture, which was maintained at 55° C. for an additional 15 minutes. Water (176 mL) was added to the reaction mixture over a 15 minute period with vigorous stirring and acetone was subsequently distilled from the mixture under reduced pressure to produce a dispersion of a silanol terminated polyurethane-urea in water.

Example 8

Preparation of Silanol Terminated Polyurethane-urea in Water

A mixture of PCPSSIP (555 g, 0.75 mol based on a hydroxyl equivalent weight of 370 for the mixture), IPDI (190.1 g, 0.86 mol), DTDL (0.36 g, 0.56 mmol), and acetone (400 g) was heated with stirring to 55° C. After 8 hours, a solution of 3-aminopropyltriethoxysilane (45.3 g, 0.20 mol) in acetone (365 g) was added to the reaction mixture, which was maintained at 55° C. for an additional 15 minutes. Water (1700 g) was added to the reaction mixture over a 15 minute period with vigorous stirring and acetone was subsequently distilled from the mixture under reduced pressure to produce a dispersion (33% solids) of a silanol terminated polyurethane-urea in water. MDSC and tensile properties analyses made of a film of the dispersion indicated that the polymer had a $T_g$ of −20° C. and a tensile strength of 975 psi at 611% elongation.

Example 9

Preparation of a Silylated Polyurethane-urea Dispersion in Water Using a Silylated Diamine with Chain-extension A mixture of PCPSSIP (47.3 g, 0.06 mol based on a hydroxyl equivalent weight of 370 for the mixture), polycaprolactone diol (14.15 g, 0.03 mol), ethylene glycol (6.71 g, 0.11 mol), 4,4'-diisocyanato dicyclohexylmethane (56.67 g, 0.22 mol), DTDL (0.09 g, 1.5 mmol) and acetone (67 mL) was heated with stirring to 60° C. After 4 hours, a solution of 3-aminopropyltriethoxysilane (4.96 g, 0.022 mol) in acetone (65 mL) was added to the reaction mixture, which was maintained at 60° C. for an additional 15 minutes. Water (200 mL) was added to the reaction mixture over a 15 minute period with vigorous stirring followed by N-(3-(trimethoxysilyl) propyl)ethylenediamine (2.50 g, 0.011 mol). The acetone was subsequently distilled from the mixture under reduced pressure to produce a dispersion of a silanol functional polyurethane-urea in water. MDSC and tensile properties analyses made of a film of the dispersion indicated that the polymer had a $T_g$ of 23° C. and a tensile strength of 3853 psi at 298% elongation.

Example 10

Preparation of a Silylated Polyurethane-urea Dispersion in Water Using a Silylated Diamine with Chain-extension A mixture of PCPSSIP (43.1 g, 0.06 mol based on a hydroxyl equivalent weight of 370 for the mixture), polycaprolactone diol (7.86 g, 0.02 mol), ethylene glycol (7.45 g, 0.12 mol), ), 4,4'-diisocyanato dicyclohexylmethane (54.94 g, 0.21 mol), DTDL (0.09 g, 1.5 mmol) and acetone (61 mL) was heated with stirring to 60° C. After 4 hours, a solution of 3-aminopropyltriethoxysilane (3.67 g, 0.017 mol) in acetone (57 mL) was added to the reaction mixture, which was maintained at 60° C. for an additional 15 minutes. Water (178 mL) was added to the reaction mixture over a 15 minute period with vigorous stirring followed by N-(3-(trimethoxysilyl) propyl)ethylenediamine (1.85 g, 0.008 mol). The acetone was subsequently distilled from the mixture under reduced pressure to produce a dispersion of a silanol functional polyurethane-urea in water. MDSC and tensile properties analyses made of a film of the dispersion indicated that the polymer had a $T_g$ of 48° C. and a tensile strength of 4775 psi at 281% elongation.

Example 11

Preparation of a Carboxylated Polyurethane-urea Dispersion

A mixture of 2,2'-bis(hydroxymethyl)propionic acid (20.1 g, 0.150 mol), polycaprolactone diol (262 g, 0.50 mol), IPDI (159 g, 0.72 mol), MEK (237 g), and DTDL (0.30 g, 0.05 mmol) was heated at reflux for 5 hours, then left at room temperature for 72 hours. The mixture was then heated at reflux for 6 more hours. An aliquot was removed for determination of isocyanate equivalent weight as described in Example 29 of U.S. Pat. No. 5,929,160. Based on the found isocyanate equivalent weight of 3,607, a solution of triethylamine (14.2 g, 0.141 mol) and 3-aminopropyltriethoxysilane (24.9 g, 0.11 mol) in MEK (232 g) was added to the reaction mixture. After stirring for an additional 15 minutes, water (1350 g) was added to the solution, and then the MEK was distilled from the mixture at reduced pressure to produce a 28% solids dispersion of the carboxylated polyurethane-urea in water.

Example 12

Preparation of Silanol Terminated Polyurethane-urea in Water

A mixture of PCPSSIP (31.41 kg, 42.5 mol based on a hydroxyl equivalent weight of 370 for the mixture), polycaprolactone diol (12.74 kg, 24.3 mol), ethylene glycol (4.03 kg, 64.8 mol), IPDI (31.8 kg, 143.1 mol), DTDL (116.0 g, 0.18 mol) and MEK (43 kg) was heated with stirring to 80 C. After 4 hours, a solution of 3-aminopropyltri-ethoxysilane (4.71 kg, 21.3 mol) in MEK (42 kg) was added to the reaction mixture, which was maintained at 80° C. for an additional 15 minutes. Water (138 kg) was added to the reaction mixture over a 15 minute period with vigorous stirring and MEK was subsequently distilled from the mixture under reduced pressure to produce a dispersion (44% solids) of a silanol terminated polyurethane-urea in water. MDSC and tensile properties analyses made of a film of the dispersion indicated that the polymer had a $T_g$ of 22° C. and a tensile strength of 4479 psi at 400% elongation.

Cosmetic Example 1

An oil-in-water sunscreen lotion was prepared from the polyurethane-urea dispersion polymer of Example 1. In separate vessels equipped with a mixing device, the components of Phase A and Phase B listed in Table I were heated to 75° C. Phase B was added to phase A. After cooling to 45° C. Phases C and D were added.

TABLE I

Oil-in-Water Sunscreen Lotion

| | % by weight |
|---|---|
| Phase A | |
| deionized water | 48.62 |
| Na₂EDTA | 0.10 |
| propylene glycol | 2.50 |
| Pemulen TR-1 (2% solution) | 10.00 |

TABLE I-continued

Oil-in-Water Sunscreen Lotion

| | % by weight |
|---|---|
| Stepanmild RM-1 | 1.50 |
| Neutrol TE | 0.40 |
| Phase B | |
| cetearyl alcohol | 1.00 |
| octyl palmitate | 5.50 |
| Z-Cote HP-1 | 6.00 |
| Lipomulse 165 | 2.00 |
| Uvinul MC80 | 7.50 |
| Octocrylene | 9.00 |
| Phase C | |
| Polyurethane-urea dispersion of Example 1 | 4.88 |
| Phase D | |
| Germaben II | 1.00 |
| Total Weight | 100.00 |

Cosmetic Example 2

An oil-in-water mascara was prepared as follows. In separate vessels equipped with a mixing device, the components of Phase A and Phase B listed in Table II were heated to 87° C. Phase B was added slowly to phase A while homogenizing. After agitating 15 minutes, the batch was cooled to 45° C., Phases C and D were added.

TABLE II

Oil-in-Water Mascara

| | % by weight |
|---|---|
| Phase A | |
| deionized water | 40.80 |
| PVP K-30 | 1.00 |
| propylene glycol | 5.00 |
| Natrosol 250 MR, HEC | 0.20 |
| black iron oxide | 10.00 |
| triethanol amine, 99% | 0.50 |
| Phase B | |
| Emersol 132, stearic acid | 4.50 |
| Glyceryl monostearate SE | 4.00 |
| white beeswax | 6.00 |
| Candelilla #1 | 3.00 |
| Carnauba #1 | 4.00 |
| Phase C | |
| Polyurethane-urea dispersion of Example 1 | 20.00 |
| Phase D | |
| Germaben II | 1.00 |
| Total Weight | 100.00 |

Cosmetic Example 3

A hydroalcoholic nail lacquer was prepared by mixing 40 weight percent of the polyurethane-urea dispersion polymer of Example 2 with 10 weight percent of the polyurethane-urea dispersion polymer of Example 8 and diluting with 50 weight percent of absolute ethanol to give a fast-drying, glossy, non-tacky nail lacquer that exhibited excellent chip resistance.

Cosmetic Example 4

A body wash lotion with good foam characteristics and that tightens the skin after rinsing was prepared as follows. Into a vessel equipped with a mixing device, the components of Phase A listed in Table III were heated to 75° C. After agitating 15 minutes, the batch was cooled to 45° C. and Phase B was added.

TABLE III

Body Wash Lotion

| | % by weight |
|---|---|
| Phase A | |
| deionized water | 16.30 |
| Standapol A | 35.70 |
| Standapol EA-2 | 24.00 |
| ethylene glycol distearate | 3.00 |
| Cocamide MEA | 1.00 |
| Phase B | |
| Polyurethane-urea dispersion of Example 11 | 20.00 |
| Total Weight | 100.00 |

Cosmetic Example 5

A shampoo with good foam characteristics and that provides fast drying and body to hair was prepared as follows. Into a vessel equipped with a mixing device, the components of Phase A listed in Table IV were heated to 75° C. After agitating 15 minutes, the batch was cooled to 45° C. and Phase B was added.

TABLE IV

Shampoo

| | % by weight |
|---|---|
| Phase A | |
| deionized water | 28.60 |
| Miranol CS | 22.20 |
| Incronam 30 | 17.10 |
| PEG 150 tetrastearate | 0.80 |
| cetyl alcohol | 0.42 |
| stearyl alcohol | 0.18 |
| Standapol EA-2 | 8.00 |
| ethylene glycol distearate | 2.00 |
| Cocamide MEA | 0.70 |
| Phase B | |
| Polyurethane-urea dispersion of Example 4 | 20.00 |
| Total Weight | 100.00 |

Cosmetic Example 6

An oil-in-water lotion was prepared as follows. Into separate vessels equipped with mixing devices, the components of Phase A and Phase B listed in Table V were heated to 75° C. While agitating Phase A with a rotor/stator homogenizer, Phase B was slowly added. After homogenizing for 10 minutes, the batch was removed from heat and allowed to slowly cool to room temperature with agitation adding Phase C.

TABLE V

Oil-in-water Lotion

| | % by weight |
|---|---|
| Phase A | |
| Water | 57.1 |
| Polyurethane-urea dispersion of Example 10 | 10.3 |
| Glycerin | 5.0 |
| Tween ™ 80 | 2.1 |
| Triethanol amine | 0.7 |
| Phase B | |
| Jojoba Oil | 14.9 |
| Octadecamethylcyclotetrasiloxane | 5.4 |
| Steric acid | 2.5 |
| Arlace ™ C | 1.0 |
| Octadecanol | 1.0 |
| Phase C | |
| Methyl paraben | 0.10 |
| Propyl paraben | 0.02 |
| Total | 100 |

Cosmetic Example 7

An water-in-oil lotion was prepared as in Cosmetic Example 6 using the components listed in Table VI except there was no Phase C in this example.

TABLE VI

Water-in-oil Lotion

| | % by weight |
|---|---|
| Phase A | |
| octadecamethylcyclotetrasiloxane | 29.5 |
| mineral oil | 17.9 |
| 3M brand Silicones "Plus" Polymer SA 70 in D5 | 12.0 |
| Abil ™ EM90 | 0.6 |
| Phase B | |
| water | 35.9 |
| Polyurethane-urea dispersion of Example 12 | 4.0 |
| methyl paraben | 0.1 |
| Total | 100 |

Cosmetic Example 8

A liquid foundation was prepared according to the procedures described in Cosmetic Example 6 using the components listed in Table VII except there was no Phase C in this example.

TABLE VII

Liquid Foundation

| | % by weight |
|---|---|
| Phase A | |
| water | 50.8 |
| propylene glycol | 10.5 |
| Monosil ™ PLN | 3.0 |
| Lauriciden ™ | 2.2 |
| triethanol amine | 1.0 |
| Rhapsody ™ 1M | 2.0 |
| Veegum | 1.1 |
| titanium dioxide #70429 | 1.0 |
| yellow iron oxide #70422 | 1.0 |
| red iron oxide #70421 | 0.9 |
| FD&C yellow 6 | 0.1 |
| ethyl paraben | 0.05 |
| propyl paraben | 0.02 |
| Polyurethane-urea dispersion of Example 9 | 7.0 |
| Phase B | |
| Finsolv ™ TN | 16.7 |
| stearic acid | 2.1 |
| Brij ™ 30 | 0.1 |
| teatree oil | 0.2 |
| Silicone Based Witch Hazel Extract | 0.2 |
| Total | 100 |

Cosmetic Example 9

An aqueous nail polish was prepared by mixing 69.45 weight percent of the polyurethane-urea dispersion polymer of Example 12 with 28.92 weight percent of the polyurethane-urea dispersion polymer of Example 2, adding 0.54 weight percent FD&C Yellow #6 and 1.09 weight percent Phenonip to give a glossy, non-tacky nail polish from which the yellow dye did not leach.

Cosmetic Example 10

A hydroalcoholic nail polish was prepared as follows. A solution of neutralized 3M brand Silicones "Plus" Polymer VS-80 was prepared by dissolving 14 weight percent VS-80 in a mixture of 50 weight percent absolute ethanol and 5.6 weight percent water and adding a solution of 0.8 weight percent concentrated ammonium hydroxide in 29.6 weight percent water. A 10.3 weight percent of this solution was combined with 63.5 weight percent of the polyurethane-urea dispersion polymer of Example 11 and 25.4 weight percent absolute ethanol, adding 0.2 weight percent FD&C Blue #6 and 0.5 weight percent methyl paraben to give a glossy, non-tacky nail polish from which the blue dye does not leach.

Cosmetic Example 11

An aqueous nail polish was prepared as follows. A solution of neutralized 3M brand Silicones "Plus" Polymer VS-80 was as in Cosmetic Example 10. A 12.8 weight percent of this solution was combined with 86.4 weight percent of the polyurethane-urea dispersion polymer of Example 12, adding 0.3 weight percent FD&C Blue #6 and 0.5 weight percent methyl paraben to give a glossy, non-tacky nail polish from which the blue dye did not leach.

Cosmetic Example 12

An aqueous nail polish was prepared as follows. A solution of Carbopol 974 was prepared by dissolving 1.22 weight percent in 98.8 weight percent water and adding concentrated ammonium hydroxide to give a pH of 6.9 to 7.1. 13.6 weight percent of this solution was combined with 83.2 weight percent of the polyurethane-urea dispersion polymer of Example 12, adding 1.8 weight percent FD&C Blue #5 and 1.4 weight percent methyl paraben to give a glossy, non-tacky nail polish from which the yellow dye did not leach.

All references cited herein, including those listed in the Background section, are incorporated by reference in each reference's entirety.

What is claimed is:

1. A method of using a cosmetic article comprising:
   (a) providing a cosmetic article containing a cosmetic composition which cosmetic composition contains in a dispensible form an aqueous dispersion of at least one polyurethane-urea polymer that is functionalized with at least one silyl containing component selected from the group consisting of:

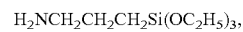

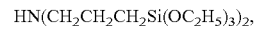

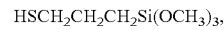

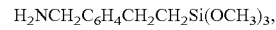

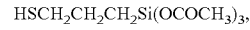

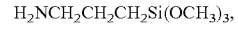

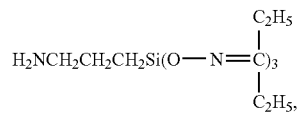

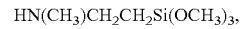

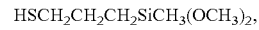

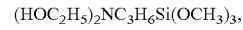

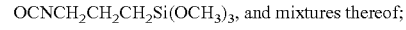, and mixtures thereof;

(b) applying said cosmetic article to a person's skin or nails; and
   (c) forming a film.

2. The method of use of claim 1 wherein said film exhibits self-adhesion properties when coated and dried to a film of about 0.025 millimeter in thickness.

3. The method of use of claim 1 wherein said cosmetic article further comprising ingredients selected from the group consisting of emollients, humectants, film forming polymers, propellants, pigments, dyes, buffers, organic suspending agents, inorganic suspending agents, organic thickening agents, inorganic thickening agents, waxes, surfactants, plasticizers, preservatives, flavoring agents, perfumes, sunscreen agents, insect repellents, vitamins, herbal extracts, skin bleaching agents, skin coloring agents, antiperspirant agents, deodorant agents, depilating agents, antifungal agents, antimicrobial agents, antiacne agents, astringents, corn removers, callus removers and wart removers.

4. A method of use of claim 1 wherein the cosmetic article comprises at least one of (a) creams, emulsions, lotions, gels, and oils for the skin; (b) face masks; (c) tinted bases; (d) make-up powders, after-bath powders, hygienic powders: (e) toilet soaps, deodorant soaps: (f) perfumes, toilet waters, cologne; (g) bath and shower preparations; (h) deodorants and anti-perspirants; (i) products for making-up and removing make-up from the face and the eyes; (j) products intended for application to the lips; (k) products for nail care and nail make-up; (l) products for external intimate hygiene; (m) sunbathing products; (n) products for tanning without sun; (o) skin-whitening products; and (p) anti-wrinkling products.

5. A method of using a cosmetic article comprising:
   (a) providing a cosmetic article containing a cosmetic composition which cosmetic composition contains in a dispensable form an aqueous dispersion and a reaction product of
      (i) at least one isocyanate terminated polyurethane-urea prepolymer derived from the reaction of at least one polyisocyanate and at least one polyol,
      (ii) at least one polyfunctional chain extender,
      (iii) at least one silyl containing component selected from the group consisting of $H_2NCH_2CH_2CH_2Si(OC_2H_5)_3$, $HN(CH_2CH_2CH_2Si(OC_2H_5)_3)_2$, $HSCH_2CH_2CH_2Si(OCH_3)_3$, $HO(C_2H_4O)_3C_2H_4N(CH_3)(CH_2)_3Si(OC_4H_9)_3$, $H_2NCH_2C_6H_4CH_2CH_2Si(OCH_3)_3$, $HSCH_2CH_2CH_2Si(OCOCH_3)_3$, $H_2NCH_2CH_2CH_2Si(OCH_3)_3$,

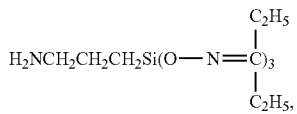

$HN(CH_3)CH_2CH_2Si(OCH_3)_3$, $HSCH_2CH_2CH_2SiCH_3(OCH_3)_2$, $(HOC_2H_5)_2NC_3H_6Si(OCH_3)_3$, $H_2NCH_2CH_2CH_2NHCH_2CH_2CH_2Si(OCH_3)_3$, $OCNCH_2CH_2CH_2Si(OCH_3)_3$, and mixtures thereof; and
   (iv) at least one hydrophilic component comprising at least one of an ionic group, a moiety capable of forming an ionic group, and a nonionic water soluble group;
   (b) applying said cosmetic article to a person's skin or nails; and
   (c) forming a film.

6. The method of use of claim 5, wherein said polyisocyanate is a diisocyanate.

7. The method of use of claim 5, wherein said polyol is a diol.

8. The method of use of claim 5, wherein said polyol has a number average molecular weight between about 200 and 5,000.

9. The method of use of claim 5 wherein said polyfunctional chain extender is selected from the group consisting of water; ethylenediamine; 1,6-diaminohexane; piperazine: tris (2-aminoethyl)amine; amine terminated polyethers; adipic acid dihydrazide; oxalic acid dihydrazide; ethylene glycol; 1,4-butane diol; 1,8octane diol; 1,2-ethanedithiol: 1,4-butanedithiol: 2,2'-oxytris(ethane thiol); di- and tri-mercaptopropionate esters of poly(oxyethylene) diols and triols; and mixtures thereof.

10. The method of use of claim 5, wherein said hydrophilic component comprises

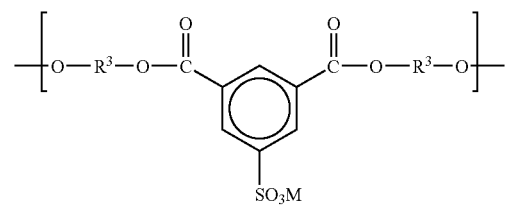

wherein each $R^3$ is independently a divalent aliphatic group having an average molecular weight of 200 to 600 comprising ether or ester functional groups selected from the group consisting of: $—CH_2CH_2—(OCH_2CH_2—)_n—$, $—CH(CH_3)CH_2—(OCH(CH_3)CH_2—)_n—$, $—(CH_2)_4—(O(CH_2)_4)_n—$, $—(CH_2)_mCO—[O(CH_2)mCO]_n—$ groups, and mixtures thereof, where m is an integer, from about 2 to 5 and n is an integer from about 2 to 15, and M is a cation selected from the group consisting of Na, H, K, Li, primary, secondary, tertiary, quaternary ammonium cation and mixtures thereof.

11. The method of use claim 5, wherein said hydrophilic component is a cationic compound having the following structure:

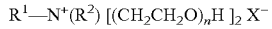

wherein $R^1$ is $C_1$ to $C_{18}$ alkyl or $C_6$ to $C_{18}$ aryl or aralkyl optionally substituted in and/or on the chain by N, O, S and combinations thereof;

$R^2$ is hydrogen or $C_1$ to $C_{18}$ alkyl;

n is an integer from about 1 to 200; and

X is halogen, sulfate, methosulfate, ethosulfate, acetate, carbonate, or phosphate.

12. The method of use of claim 5 wherein said him exhibits self-adhesion properties when coated and dried to a film of about 0.025 millimeter in thickness.

13. A method of using a cosmetic article comprising:
   (a) providing a cosmetic article containing a cosmetic composition which cosmetic composition contains in a dispensable form an aqueous dispersion and a reaction product of
      (i) at least one isocyanate terminated polyurethane-urea prepolymer derived from the reaction of at least one polyisocyanate, and at least one polyol;
      (ii) at least one polyfunctional chain extender;
      (iii) at least silyl containing component having the formula $(R^4O)_3SiR^5Z$ wherein $R^4$ is a lower alkyl radical of one to four carbon atoms or lower acyl of two to five carbon atoms, $R^5$ is a divalent organic bridging radical of 2 to 20 carbon atoms selected from the group consisting of a divalent hydrocarbyl radical free from olefinic unstauration and free from isocyanate-reactive groups, a divalent polyoxyalkylene mono- or poly-oxaalkylene radical containing not more than one ether oxygen per two carbon atoms or a divalent hydrocarbylamino radical, and Z is —OH, —N(C$_2$H$_4$OH)$_2$, —NCO or epoxide, and (iv) at least one hydrophilic component comprising at least one of an ionic group, a moiety capable of forming an ionic group, and a nonionic water soluble group;

(b) applying said cosmetic article to a person's skin or nails; and (c) forming a film.

14. The method of use of claim 13, wherein said polyisocyanate is a diisocyanate.

15. The method of use of claim 13, wherein said polyol is a diol.

16. The method of use of claim 13, wherein said polyol has a number average molecular weight between about 200 and 5,000.

17. The method of use of claim 13, wherein said chain extender is selected from the group consisting of water; ethylenediamine; 1,6-diaminohexane; piperazine; tris(2-aminoethyl)amine; amine terminated polyethers; adipic acid dihydrazide; oxalic acid dihydrazide; ethylene glycol; 1,4-butane diol; 1,8-octane diol; 1,2-ethanedithiol: 1,4-butanedithiol; 2,2'oxytris(ethane thiol); di- and tri-mercaptopropionate esters of poly(oxyethylene) diols and triols; and mixtures thereof.

18. The method of use of claim 13, wherein said hydrophilic component comprises

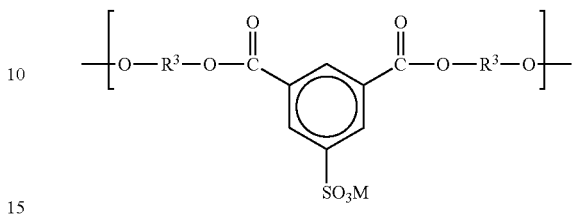

wherein each $R^3$ is independently a divalent aliphatic group having an average molecular weight of 200 to 600 comprising ether or ester functional groups selected from the group consisting of: —CH$_2$CH$_2$—(OCH$_2$CH$_2$—)$_n$—, —CH(CH$_3$)CH$_2$—(OCH(CH$_3$)CH$_2$—)$_n$—, —(CH$_2$)$_4$—(O(CH$_2$)$_4$)$_n$—, —(CH$_2$)$_m$CO—[O(CH$_2$)mCO]$_n$— groups, and mixtures thereof, where m is an integer, from about 2 to 5 and n is an integer from about 2 to 15, and M is a cation selected from the group consisting of Na, H, K, Li, primary, secondary, tertiary, quaternary ammonium cation and mixtures thereof.

* * * * *

UNITED STATES PATENT AND TRADEMARK OFFICE
CERTIFICATE OF CORRECTION

PATENT NO. : 7,700,082 B2  Page 1 of 3
APPLICATION NO. : 09/771054
DATED : April 20, 2010
INVENTOR(S) : Richard A. Mallo It is certified that error appears in the above-identified patent and that said Letters Patent is hereby corrected as shown below:

Column 1
Line 1, First Page, delete "Dietrich" and insert -- Dieterich --, therefor.

Column 6
Line 6-7, in Specification, delete "1,1,1 –trimethylol" and insert -- 1,1,1-trimethylol --, therefor.

Line 58-59, in Specification, delete "1,2-decandiol." and insert -- 1,2-decanediol. --, therefor.

Column 8
Line 25 (approx.), in Specification, delete
"—(CH$_2$)$_m$CO—[O(CH$_2$)$_m$CO]$_n$—groups; and" and insert
-- —(CH$_2$)$_m$CO—[O(CH$_2$)$_m$CO]$_n$— groups; and --, therefor.

Column 10
Line 34, in Specification, delete "arnines" and insert -- amines --, therefor.

Column 12
Line 18, in Specification, delete "Phillipsburgh," and insert -- Phillipsburg, --, therefor.

Line 38, in Specification, delete "Phillipsburgh," and insert -- Phillipsburg, --, therefor.

Line 42, in Specification, delete "Coming," and insert -- Corning, --, therefor.

Line 43, in Specification, delete "Gambel," and insert -- Gamble, --, therefor.

Line 47, in Specification, delete "Dansbury," and insert -- Danbury, --, therefor.

Column 13
Line 18, in Specification, delete "Lauriciden™" and insert -- Lauricidin™ --, therefor.

Line 36, in Specification, delete "Vanderbelt," and insert -- Vanderbilt, --, therefor.

Signed and Sealed this

Twenty-ninth Day of June, 2010

David J. Kappos
*Director of the United States Patent and Trademark Office*

Column 14
Line 62, in Specification, delete "(80 niL)" and insert -- (80 mL) --, therefor.

Column 15
Line 5, in Specification, After "of" delete "15".

Column 17
Line 36, in Specification, delete "3-aminopropyltri-ethoxysilane" and insert
-- 3-aminopropyltriethoxysilane --, therefor.

Column 18
Line 51, in Specification, delete "Camauba" and insert -- Carnauba --, therefor.

Column 20
Line 23, in Specification, delete "Steric" and insert -- Stearic --, therefor.

Line 24, in Specification, delete "Arlace™" and insert -- Arlacel™ --, therefor.

Column 21
Line 11, in Specification, delete "Lauriciden™" and insert -- Lauricidin™ --, therefor.

Column 22
Line 34 (approx.), in Claim 1, delete
"HO(C$_2$H$_4$O)$_3$C$_2$H$_4$N(CH$_3$(CH$_2$)$_3$Si(OC$_4$H$_9$)$_3$," and insert
-- HO(C$_2$H$_4$O)$_3$C$_2$H$_4$N(CH$_3$)(CH$_2$)$_3$Si(OC$_4$H$_9$)$_3$, --, therefor.

Line 40-47 (approx.), in Claim 1, delete " 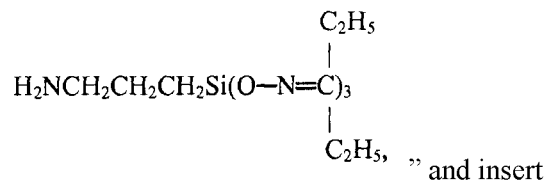 " and insert
-- 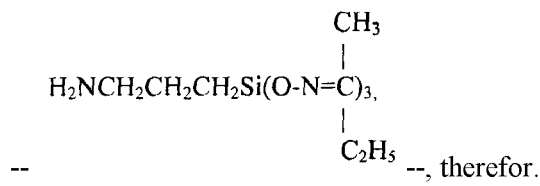 --, therefor.

Column 23
Line 11, in Claim 4, delete "powders:" and insert -- powders; --, therefor.

Line 12, in Claim 4, delete "soaps:" and insert -- soaps; --, therefor.

Line 45-50 (approx.), in Claim 5, delete " 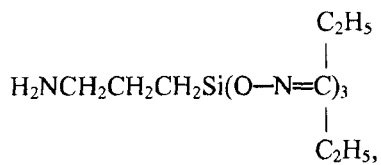 " and insert

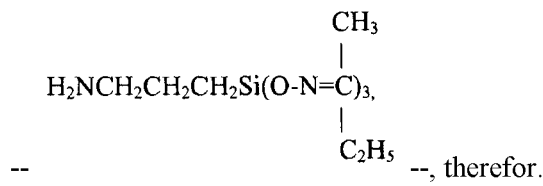 --, therefor.

Line 58 (approx.), in Claim 5, delete "thereof;" and insert -- thereof, --, therefor.

Column 24
Line 8, in Claim 9, after "claim 5" insert -- , --.

Line 10, in Claim 9, delete "piperazine:" and insert -- piperazine; --, therefor.

Line 13, in Claim 9, delete "1,8octane diol; 1,2-ethanedithiol:" and insert
-- 1,8-octane diol; 1, 2-ethanedithiol; --, therefor.

Line 35, in Claim 10, delete "—$(CH_2)_mCO$—$[O(CH_2)mCO]_n$—" and insert
-- —$(CH_2)_mCO$—$[O(CH_2)_mCO]_n$— --, therefor.

Line 54, in Claim 12, delete "him" and insert -- film --, therefor.

Line 66, in Claim 13, after "least" insert -- one --.

Column 25
Line 5, in Claim 13, delete "unstauration" and insert -- unsaturation --, therefor.

Line 30, in Claim 17, delete "1,2-ethanedithiol:" and insert -- 1,2-ethanedithiol; --, therefor.

Column 26
Line 1, in Claim 17, delete "2,2'oxytris(ethane thiol);" and insert
-- 2,2'-oxytris(ethane thiol); --, therefor.

Line 22, in Claim 18, delete "—$(CH_2)_mCO$—$[O(CH_2)mCO]_n$—" and insert
-- —$(CH_2)_mCO$—$[O(CH_2)_mCO]_n$— --, therefor.

Line 23, in Claim 18, delete "integer," and insert -- integer --, therefor.